United States Patent
Kohlstruk et al.

(10) Patent No.: US 6,495,650 B2
(45) Date of Patent: Dec. 17, 2002

(54) 1,4-DIISOCYANATO-2,2,6-TRIMETHYLCYCLOHEXANE POLYISOCYANATES CONTAINING ISOCYANURATE GROUPS, A PROCESS FOR THE PREPARATION AND USE

(75) Inventors: Stephan Kohlstruk, Marl (DE); Emmanouil Spyrou, Marl (DE); Klaus Pinske, Haltern (DE)

(73) Assignee: Degussa AG, Duesseldorf (DE)

( * ) Notice: Subject to any disclaimer, the term of this patent is extended or adjusted under 35 U.S.C. 154(b) by 36 days.

(21) Appl. No.: 09/819,664

(22) Filed: Mar. 29, 2001

(65) Prior Publication Data

US 2001/0027243 A1 Oct. 4, 2001

(30) Foreign Application Priority Data

Mar. 30, 2000 (DE) .......................................... 100 15 890

(51) Int. Cl.$^7$ ........................ C08G 18/79; C08G 18/80; C07D 251/34
(52) U.S. Cl. ........................... 528/45; 528/73; 544/193; 544/222

(58) Field of Search .................... 528/45, 73; 544/193, 544/222

(56) References Cited

U.S. PATENT DOCUMENTS

| | | | |
|---|---|---|---|
| 4,246,380 A | | 1/1981 | Gras .......................... 525/440 |
| 5,691,440 A | * | 11/1997 | Katz et al. .................... 528/52 |
| 6,242,641 B1 | * | 6/2001 | Jautelat et al. ................ 60/330 |

FOREIGN PATENT DOCUMENTS

| EP | 0 945 427 | | 9/1999 |
|---|---|---|---|
| EP | 945427 | * | 9/1999 |

OTHER PUBLICATIONS

J. Appl. Polym. Sci. 1994, 54(2), 207–218.

* cited by examiner

Primary Examiner—Rabon Sergent
(74) Attorney, Agent, or Firm—Oblon, Spivak, McClelland, Maier & Neustadt, P.C.

(57) ABSTRACT

The invention provides polyisocyanates containing isocyanate groups from 1,4-diisocyanato-2,2,6-trimethylcyclohexane, having a trimer fraction of more than 80% by weight and an NCO content of at least 19.3%.

13 Claims, No Drawings

1,4-DIISOCYANATO-2,2,6-TRIMETHYLCYCLOHEXANE POLYISOCYANATES CONTAINING ISOCYANURATE GROUPS, A PROCESS FOR THE PREPARATION AND USE

BACKGROUND OF THE INVENTION

1. Field of the Invention

The invention relates to a novel polyisocyanate from 1,4-diisocyanato-2,2,6-trimethylcyclohexane (TMCDI) which contains isocyanurate groups, to a process for the preparation, and to the use.

2. Discussion of the Background

Aliphatic and cycloaliphatic diisocyanates are widely employed in high-grade light-and weather-stable polyurethane coatings. For many applications, such as for trimerization, for example, it is advantageous for the two isocyanate groups to differ in reactivity. By virtue of this so-called selectivity the fraction of unwanted oligomers (pentamers, heptamers, nonamers, etc.) is reduced and the resulting products (polyisocyanates containing isocyanurate groups) have higher NCO contents, lower viscosities and improved technical processability.

Hexamethylene diisocyanate (HDI) exhibits no selectivity whatsoever and so the corresponding polyisocyanate containing isocyanurate groups has a high unwanted oligomer fraction. Isophorone diisocyanate (IPDI), on the other hand, is selective owing to the different stearic environment of the two isocyanate groups, but trimerization under the same conditions leads to relatively low unwanted oligomer contents of approximately 35% by weight and a trimer fraction of approximately 65% by weight.

The object was to find a trimeric isocyanate having a higher NCO content and improved, lower viscosity. This object has been achieved by the trimerization product of TMCDI, with a trimer fraction of more than 80% by weight and an NCO content of at least 19.3% by weight of the trimerization product.

It has surprisingly been found that 1,4-diisocyanato-2,2,6-trimethylcyclohexane (TMCDI), a readily available cycloaliphatic diisocyanate (J. Appl. Polym. Sci. 1994, 54(2), 207–218; EP 0 945 427 A1) is particularly suited to trimerization. For a given conversion, the unwanted oligomer content of the resulting polyisocyanates containing isocyanurate groups is distinctly lower than in the case of polyisocyanates based on IPDI and containing isocyanurate groups, and the NCO content is distinctly higher.

SUMMARY OF THE INVENTION

The invention provides polyisocyanates containing isocyanurate groups from 1,4-diisocyanato-2,2,6-trimethylcyclohexane, having a trimer fraction of more than 80% by weight preferably more than 90% by weight and an NCO content of at least 19.3%, preferably at least 19.6% by weight.

The invention further provides a process for preparing polyisocyanates containing isocyanurate groups from 1,4-diisocyanato-2,2,6-trimethylcyclohexane, having a trimer fraction of more than 80% by weight, preferably more than 90% by weight, and an NCO content of at least 19.3%, preferably at least 19.6% by weight, by reacting TMCDI in the presence of at least one trimerization catalyst at from 70 to 150° C.

DETAILED DESCRIPTION OF THE PREFERRED EMBODIMENTS 1,4-Diisocyanato-2,2,6-trimethylcyclohexane, referred to below simply as TMCDI, may be converted into a polyisocyanate containing isocyanurate groups by trimerization in the presence of appropriate catalysts. For this purpose, a catalyst is added to TMCDI at room temperature and the system is heated at 130° C. After twenty minutes, depending on the amount of catalyst, the reaction has progressed to a conversion of approximately 30–60% and is terminated either thermally or by adding an acid. Excess diisocyanate is distilled off at 150° C. and 0.1 mbar in a short-path evaporator. The resulting polyisocyanates containing isocyanurate groups have an unwanted oligomer fraction of 8–20% by weight (trimer fraction 92–80% by weight) and an NCO content of 19.3–20.0% by weight.

Non-limiting examples of suitable trimerization catalysts are quaternary ammonium carboxylates, alkali metal and alkaline earth metal salts of carboxylic acids, trialkylphosphines or quaternary ammonium carbonates or amino silane compounds. Trioctylmethylammonium 2-ethylhexanoate, for example, is particularly suitable, and may be prepared from the corresponding chloride by the method described in more detail in U.S. Pat. No. 5,691,440.

TMCDI-based polyisocyanates containing isocyanurate groups, possibly in blocked form, represent valuable starting materials for preparing polyurethane plastics by the isocyanate polyaddition process, as base materials for coatings, and especially for preparing one- or two-component polyurethane coating materials.

Suitable blocking agents are known within isocyanate chemistry, examples being ethyl acetoacetate, diisopropylamine, methyl ethyl ketoxime, diethyl malonate, E-caprolactam, 1,2,4-triazole, and 3,5-dimethylpyrazole.

Having generally described this invention, a further understanding can be obtained by reference to certain specific examples which are provided herein for purposes of illustration only and are not intended to be limiting unless otherwise specified. The examples which follow are intended to illustrate, but not restrict, the invention:

Preparation of a polyisocyanate containing isocyanurate groups from 1,4-diisocyanato-2,2,6-trimethylcyclohexane.

292 g of 1,4-diisocyanato-2,2,6-trimethylcyclohexane were introduced into a reaction vessel, 1.46 g of trioctylmethylammonium 2-ethylhexanoate were added, and the system was heated at 130° C. under insert gas and with stirring. After 20 minutes, the temperature was raised briefly to 150° C. and the system was then cooled (NCO content: 31.3%, 45% conversion). Excess TMCDI was separated off on a short-path evaporator at 150° C. and 0.1 mbar. The demonomerized product had an NCO content of 19.8% and an unwanted oligomer fraction of 33% (trimer fraction 92%) (gel permeation chromatography (GPC), super-fluid chromatography (SFC)).

COMPARATIVE EXAMPLE

Preparation of a Polyisocyanate Containing Isocyanurate Groups from Isophorone Diisocyanate 286 g of isophorone diisocyanate were introduced into a reaction vessel, 0.25 g of trioctylmethylammonium 2-ethylhexanoate were added, and the system was heated at 70° C. under inert gas and with stirring. After this initiation, the temperature of the exothermic reaction passed through a maximum and then fell back (NCO content: 29.1%, 46% conversion). Excess IPDI was separated off on a short-path evaporator at 150° C. and 0.1 mbar. The demonomerized product had an NCO content of 17.4% and an unwanted oligomer fraction of 33% (tiimer fraction 67%) (GPC, SFC).

Obviously, numerous modifications and variations of the present invention are possible in light of the above teachings. It is therefore to be understood that within the scope of the appended claims, the invention may be practiced otherwise than as specifically described herein.

This application is based on German patent application 10015890.0 filed in the German Patent Office on Mar. 30, 2000 the entire contents of which are hereby incorporated by reference.

What is claimed is:

1. A polyisocyanate composition which is a polyisocyanate comprising isocyanurate groups from the diisocyanate 1,4-diisocyanato-2,2,6-trimethylcyclohexane, the polyisocyanate composition having a 1,4-diisocyanato-2,2,6-trimethylcyclohexane trimer fraction of more than 80% by weight of the polyisocyanate composition and an NCO content of at least 19.3% by weight of the polyisocyanate composition, the balance of the polyisocyanate composition being a 1,4-diisocyanato-2,2,6-trimethylcyclohexane oligomer fraction other than the trimer fraction.

2. The polyisocyanate composition comprising isocyanurate groups of claim 1, wherein said trimer fraction is more than 90% by weight of the polyisocyanate composition, with an NCO content of at least 19.6% by weight of the polyisocyanate composition.

3. The process of preparing the polyisocyanate composition of claim 2 which comprises reacting 1,4-diisocyanato-2,2,6-trimethylcyclohexane in the presence of a trimerization catalyst at from 70 to 150° C. and distilling of the excess 1,4-diisocyanato-2,2,6-trimethylcyclohexane.

4. The polyisocyanate composition comprising isocyanurate groups of claim 1, which has been blocked by a blocking agent.

5. The polyisocyanate composition comprising isocyanurate groups of claim 4, wherein said blocking agent is selected from the group consisting of ethyl acetoacetate, diisopropylamine, methyl ethyl ketoxime, diethyl malonate, ε-caprolactam, 1,2,4-triazole, 3,5-dimethylpyrazole and mixtures thereof.

6. A one- or two-component polyurethane coating material comprising the polyisocyanate composition of claim 1 or the polyisocyanate composition of claim 1 blocked by a blocking agent.

7. A process for preparing a polyisocyanate composition containing isocyanaurate groups from 1,4-diisocyanato-2,2,6-dimethylcyclohexane, having a trimer fraction of more than 80% by weight and an NCO content of at least 19.3% by weight of the polyisocyanate composition, balance being an oligomer fraction other than the trimer fraction, which comprises reacting 1,4-diisocyanato-2,2,6-trimethylcyclohexane in the presence of at least one trimerization catalyst at from 70 to 150° C. and distilling off excess 1,4-diisocyanato-2,2,6-trimethylcyclohexane.

8. The process of claim 7, wherein said catalyst is selected from the group consisting of quaternary ammonium carboxylates, alkali metal and alkaline earth metal salts of carboxylic acids, trialkylphosphines, quaternary ammonium carbonates and aminosilane compounds.

9. The process of claim 8, wherein said catalyst is trioctylmethylammonium 2-ethylhexanoate.

10. A method of coating comprising the step of applying to a surface the polyisocyanate composition comprising the trimer of the diisocyanate 1,4, diisocyanato-2,2,6-trimethylcyclohexane said polyisocyanate composition having a trimer fraction of more than 80% by weight of the polyisocyanate composition, and a NCO content of at least 19.3% by weight of the polyisocyanate composition the balance of the polyisocyanate composition being an oligomer of the diIsocyanate other than the trimer.

11. The method of coating according to claim 10 comprising the step of applying to a surface the polyisocyanate composition comprising the trimer of the diisocyanate 1,4-diisocyanato-2,2,6-trimethylcyclohexane, the polyisocyanate composition having a trimer fraction of more than 90% by weight of the polyisocyanate composition and a NCO content of at least 19.6% by weight of the polyisocyanate composition, the balance of the polyisocyanate composition being an oligomer of the diisocyanate other than the trimer.

12. A polyurethane comprising the reaction product of a polyisocyanate composition which is a polyisocyanate comprising isocyanurate groups from the diisocyanate 1,4-diisocyanato-2,2,6-trimethylcyclohexane, the polyisocyanate composition having a trimer fraction of more than 80% by weight of the polyisocyanate composition and an NCO content of at least 19.3% by weight of the polyisocyanate composition, the balance of the polyisocyanate composition being an oligomer of the diisocyanate other than the trimer.

13. A polyurethane comprising the reaction product of a polyisocyanate composition which is a polyisocyanate comprising isocyanurate groups from the diisocyanate 1,4-diisocyanato-2-2,6-trimethylcyclohexane, the polyisocyanate composition having a trimer fraction of more than 90% by weight of the polyisocyanate composition and an NCO content of at least 19.6% by weight of the polyisocyanate composition, the balance of the polyisocyanate composition being an oligomer of the diisocyanate other than the trimer.

* * * * *